(12) United States Patent
Keen

(10) Patent No.: US 8,015,032 B2
(45) Date of Patent: Sep. 6, 2011

(54) BROADCASTING MEDICAL IMAGE OBJECTS WITH DIGITAL RIGHTS MANAGEMENT

(75) Inventor: Ronald Keen, Shelbourne, VT (US)

(73) Assignee: General Electric Company, Schenectady, NY (US)

( * ) Notice: Subject to any disclaimer, the term of this patent is extended or adjusted under 35 U.S.C. 154(b) by 964 days.

(21) Appl. No.: 11/383,662

(22) Filed: May 16, 2006

(65) Prior Publication Data

US 2007/0270695 A1    Nov. 22, 2007

(51) Int. Cl.
*G06Q 50/00* (2006.01)
(52) U.S. Cl. .............................. 705/3; 705/2
(58) Field of Classification Search .......... 705/2, 3
See application file for complete search history.

(56) References Cited

U.S. PATENT DOCUMENTS

| | | | |
|---|---|---|---|
| 6,725,274 B1 | 4/2004 | Slik | |
| 7,028,071 B1 | 4/2006 | Slik | |
| 2002/0016922 A1* | 2/2002 | Richards et al. | 713/200 |
| 2002/0164956 A1* | 11/2002 | Maltz et al. | 455/69 |
| 2006/0242159 A1* | 10/2006 | Bishop et al. | 707/10 |

OTHER PUBLICATIONS

Maples, Bruce. "IPv6: What you need to know", TechRepublic, Apr. 11, 2000 (accessed at http://articles.techrepublic.com.com/5100-10878_11-1059598.html on Nov. 18, 2009).*
Cravotta, Robert. "Charting your course: follow the silicon-breadcrumb trail in this directory to find the prefect device for your project", 32nd, Annual Microprocessor Directory, EDN, Aug. 4, 2005.*

* cited by examiner

*Primary Examiner* — Luke Gilligan
*Assistant Examiner* — Robert Sorey
(74) *Attorney, Agent, or Firm* — Andrus, Sceales, Starke & Sawall, LLP

(57) ABSTRACT

Techniques are disclosed for efficiently and securely handling of patient medical images and data. In one particular embodiment, an acquisition service and picture archive communication system (PACS) architecture are provided that facilitate the transmission and storage of medical image objects using reliable IP multicasting, packet encoded transmission, and digital rights management (DRM). The system effectively creates a broadcast signal in which all listening computers can securely receive medical image objects at once for purposes of interpretation/diagnosis, assisting in surgery, and other such appropriate medical uses.

11 Claims, 3 Drawing Sheets

BROADCASTING MEDICAL IMAGE OBJECTS WITH DIGITAL RIGHTS MANAGEMENT

FIELD OF THE INVENTION

The invention relates to picture archive communication systems (PACS), and more particularly, to the distribution and management of medical image objects for radiology, cardiology and other specialties such as orthopedics.

BACKGROUND OF THE INVENTION

A picture archive communication system (PACS) is a system that facilitates the acquisition, storage, retrieval, distribution, and display of digital images and related patient information from a variety of imaging sources (e.g., CT scans, MRI scans, X-rays, ultrasounds, and other medical images) using a network. The network may be a local or wide-area network, and typically is configured with modality interfaces and a server system for a healthcare facility. DICOM (Digital Imaging and Communications in Medicine) is a standard that defines connectivity and communication protocols of medical imaging devices, and includes a file format definition for storing and distributing medical imaging information.

Current PACS technology utilizes point-to-point networking to move images from modality-to-DICOM acquisition, to caching server, to archive, to backup. Images are fully "copied" on and across the network many times. In addition, an end-user must copy a lossless version of the medical image to the client computer as they view the study. Such point-to-point networking and repeated copying is associated with significant bandwidth usage and time delays.

In addition, current PACS solutions must re-start transmission of the entire medical image object from the source to the client computer in the event that the connection is lost or failure occurs. Moreover, current PACS solutions require low-latency networks, since the image pixel data is typically transmitted to the client computer as it is requested. With high-latency connections, pixel data transmissions may be susceptible to unacceptable end-user wait times. Further exacerbating this situation is that current PACS solutions do not utilize the processing power and data storage available on common ordinary personal computers.

Current PACS technology requires extensive workflow rules processors to "push" studies to the intended diagnostic workstation from which the study will be viewed by a clinician, or the clinician has to "request" studies and then wait while they are transferred to their computer for viewing. PACS solutions also require costly storage area networks (SANs) to serve up images on demand. Many traditional PACS solutions require a network to be active in order to view studies. This creates significant problems and patient safety issues for patient procedure labs, and surgery rooms where imaging is required 100% of the time.

Furthermore, traditional PACS viewing stations may expose patient privileged information since DICOM studies are usually stored secondarily on PC file systems. DICOM file format includes patient confidential information and does not provide a method for securing this data. A DICOM part-10 patient medical image file can be passed around via the Internet, email, and other such common forms of communication without consent from the patient or physician. Part-15 of the DICOM specifies transmission and some negotiation security, but does not address the Part-10 file security issue.

What is needed, therefore, are techniques for efficiently distributing and securely handling of patient medical images.

SUMMARY OF THE INVENTION

One embodiment of the present invention is a method for securely communicating medical information. The method includes receiving patient information, including medical image data, converting the patient information into medical image object (MIOs), and encrypting the MIOs. The method further includes creating an issuance license that specifies access rights of the MIOs, thereby limiting future access to the MIOs. The method further includes chunking the encrypted MIOs into packets, and assigning a manifest to each chunked MIO. The method further includes broadcasting the manifest and encrypted MIO packets to a plurality of receivers on a network. The method may further include receiving the broadcast manifest and encrypted MIO packets at one or more of the receivers, and re-assembling the MIOs from instructions included in the manifest. Here, the method further includes storing the reassembled MIOs local to the at least one receiver, and requiring user authentication in accordance with the issuance license during access attempts of the stored reassembled MIOs. In one such case, the method further includes sending by each of the one or more receivers a notification to a directory service to indicate that it has received the broadcast MIOs. The method may include storing the issuance license in a digital rights management (DRM) license store of a directory service. The method may include storing the encrypted MIO packets in an archive for long term storage. The method may include indexing and tracking location of all broadcast MIOs using a directory service. In one such case, the method further includes sending by at least one of the receivers a notification to the directory service to indicate that the receiver has received the broadcast MIOs. The method may include storing the reassembled MIOs local to the at least one receiver, removing older MIOs to make room for newly received MIOs, and notifying a directory service of the change in MIO storage. In one particular case, converting the patient information into MIOs includes converting the patient information into Digital Imaging and Communications in Medicine (DICOM) MIOs. In another particular case, broadcasting the manifest and encrypted MIO packets is carried out using reliable IP multicasting.

Another embodiment of the present invention provides one or more machine-readable mediums (e.g., one or more compact disks, diskettes, servers, memory sticks, or hard drives) encoded with instructions, that when executed by one or more processors, cause the processor to carry out a process for securely communicating medical information. This process can be, for example, similar to or a variation of the previously described method.

Another embodiment of the present invention is a system for securely communicating medical information. The system functionality can be implemented, for example, in software (e.g., executable instructions encoded on one or more processor-readable storage mediums), hardware (e.g., gate level logic or one or more ASICs), firmware (e.g., one or more microcontrollers with I/O capability and embedded routines for carrying out the functionality described herein), or some combination thereof. One such system includes an acquisition service for receiving patient information including medical image data, converting the patient information into medical image object (MIOs), encrypting the MIOs, and creating an issuance license that specifies access rights of the MIOs, thereby limiting future access to the MIOs. The system further includes a packet encoder for chunking the encrypted MIOs into packets, and assigning a manifest to each chunked MIO. The system further includes a broadcast service for broadcasting the manifest and encrypted MIO packets to a plurality of receivers on a network. The system may include a receiver agent for receiving the broadcast manifest and encrypted MIO packets at one or more of the plurality of receivers, and re-assembling the MIOs from instructions included in the manifest. The system may include a storage facility for storing the reassembled MIOs local to the at least one receiver. The system may include a digital rights management (DRM) license store for use in carrying out user authentication in accordance with the issuance license during access attempts of the stored reassembled MIOs.

The features and advantages described herein are not all-inclusive and, in particular, many additional features and advantages will be apparent to one of ordinary skill in the art in view of the figures and description. Many suitable means for implementing embodiments of the present invention will be apparent in light of this disclosure. Moreover, it should be noted that the language used in the specification has been principally selected for readability and instructional purposes, and not to limit the scope of the inventive subject matter.

DETAILED DESCRIPTION OF THE INVENTION

Figure 1:
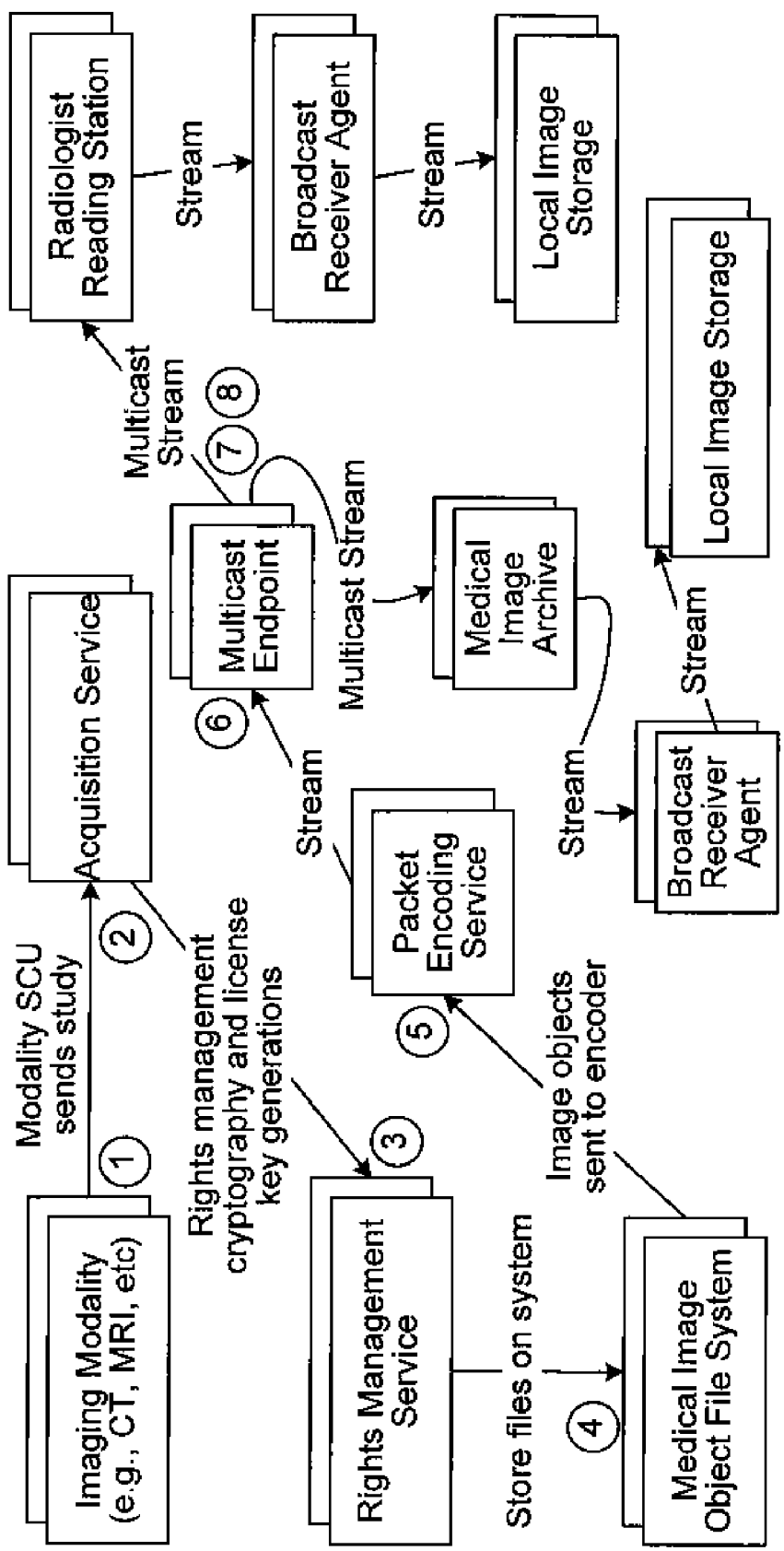
FIG. 1 is a collaboration diagram showing flow of information and processing in a picture archive communication system (PACS) configured in accordance with one embodiment of the present invention.

Techniques are disclosed for efficiently and securely handling of patient medical images and data. In one particular embodiment, an acquisition service and picture archive communication (PACS) architecture are provided that facilitate the transmission and storage of medical image objects using reliable IP multicasting, packet encoded transmission, and digital rights management (DRM). The system effectively creates a broadcast signal in which all "listening" computers can securely receive medical image objects at once for purposes of interpretation/diagnosis, assisting in surgery, and other such appropriate medical uses.

General Overview

During the acquisition process from the modality to the acquisition service, DICOM study information in rights management format (or other such format) is broadcast to all available listeners at once. This broadcast can be implemented much like an RF broadcast using IP multicasting with packet coordination/sequencing. The listeners to this broadcast information include, for example, clinician's workstations, DICOM caching servers, medical imaging archives, and offsite storage (e.g., disaster copies of the medical image objects). Devices such as clinician's workstations may keep in a local copy on disk a FIFO (first-in-first out) copy of as many medical objects as possible.

By moving medical image objects instantaneously to all points of possible care, better diagnosis/interpretation can occur since all specialists will have the medical image objects for review at once. Prior medical image objects may also be broadcast from long-term storage (e.g., PACS archive) to all points of care, so as to further facilitate better diagnosis/interpretation.

Broadcasting studies to all listeners at once creates a low-bandwidth constant stream of information, which reduces the need for point-to-point high bandwidth connections and reduces CPU/network processing and bandwidth requirements. In addition, all client computers become digital recorders of the study information, which gives the healthcare providers (e.g., interpreters/radiologists) instant access in full fidelity of the medical image objects. Furthermore, by broadcasting study information onto numerous clinician stations, there is a greatly reduced chance of loosing medical image objects due to catastrophes or hardware problems. In addition, various embodiments of the present invention reduce cost by eliminating the need for regional/localized caching servers, and also by immediately providing images, with no or negligible waiting time for the interpreters/radiologists. Moreover, note that patient care can continue during network disruptions, as the medical objects can be stored local to the interpreters/radiologists.

By using packet encoding (which effectively chunks up the medical image object into sections), re-transmission of the entire medical image object is not necessary in the event a network or other transmission failure occurs. Also packet encoding allows a receiver to pickup the packets out of sequence to avoid the broadcaster having to resend the entire medical image object. This is a particular benefit for large objects in WAN/Public VPN environments. By integrating digital rights management (DRM) into the PACS (e.g., by encrypting medical image objects with authenticable access/view rights polices), the broadcast information fully supports patient privacy, and is HIPAA-enabled. Furthermore, with the advent of the "patient owns the information," the solutions described herein support the patient controlling access while allowing for distribution. The solutions also permit changing the permissions on "rights to decrypt" and access/view from a centrally controlled rights management server (or other facility). These permissions can be time-sensitive, such that rights to decrypt/access/view only exist for periods of time (e.g., through use of an expiration date). As such, there is no need to re-send the decrypted objects or to access the remote computers to change the access rights.

A PACS configured in accordance with an embodiment of the present invention can be implemented using any number of communication technologies and network topologies. One embodiment employs WAN client workstations that include broadband (e.g., DSL/Cable) modems to communicate with other components in the PACS (e.g., where the PACS is distributed between multiple campuses and uses a communication medium that includes the Internet). Another embodiment employs a high-speed LAN configuration (e.g., Ethernet), such as that found in a large healthcare provider campus. Another embodiment employs one or more wireless networks. In short, any one or combination of network topologies can be used, as will be apparent in light of this disclosure. For example, assume the PACS is distributed over two different healthcare provider campuses that are communicatively connected via a WAN including the Internet. In addition, each campus has a LAN that includes WiFi-enabled pods that include a plurality of work/view stations.

System Dataflow

FIG. 1 is a collaboration diagram showing flow of information and processing in a picture archive communication system (PACS) configured in accordance with one embodiment of the present invention. As can be seen, the diagram is annotated with eight major steps, each of which will be described in turn. Note that the steps are not intended to implicate any particular processing order.

The imaging modality can be any one of a variety of imaging sources, such as CT scanners, MRI scanners, X-ray machines, and other such medical imaging equipment. In one particular embodiment, the imaging modality is DICOM-based. As previously explained, DICOM (Digital Imaging and Communications in Medicine) is a standard that includes a file format definition for storing and distributing medical imaging information. The DICOM standard is herein incorporated in its entirety by reference, and is also publicly available on the WWW at: http://medical.nema.org/. In general, a DICOM file includes a header with standardized as well as free-form fields and a body of image data. A single DICOM file can contain one or more images, thereby allowing for storage of volumes and/or animations. Image data can be compressed using any number of conventional or proprietary standards, such as JPEG, run-length encoding (RLE), and LZW. As is further known, DICOM groups information together into a file. For instance, a CT scan of a patient's abdomen is in the same file as the patient's ID and other patient information. A DICOM file also typically includes a media directory (DICOMDIR) that provides an index and other pertinent information for the contents of the DICOM file. Other embodiments can be implemented with other such standards and/or file formats, and the present invention is not intended to be limited to any one in particular.

In any case, step 1 shown in FIG. 1 includes the modality SCU (whether DICOM-based or other) sending the study (e.g., medical images and/or other personal medical data) to the acquisition service. In this particular embodiment, the modality is DICOM-based and transmits the study using transmission control protocol (TCP) or other suitable protocol for reliable network transmission. Here, at step 2, the acquisition service is programmed or otherwise configured to convert the TCP stream of data into DICOM objects.

At step 3, the rights management service is programmed or otherwise configured to determine the correct owner of the DICOM objects based on the information in the DICOM header of the objects. This header information includes, for example, patient, provider, addresses, medical record number, exam accession number, etc. From this information, the rights management service is programmed or otherwise configured to assign an encryption key against the objects based upon the registered owner. This registered owner could be the patient associated with the content, but most likely would be the provider who requested the procedure (or both). Objects are encrypted, and keys are registered in the medical image archive/license store.

In step 4, the encrypted objects are written to a medical image object file system. Any number of conventional or custom encryption techniques (e.g., symmetrical/asymmetrical key and/or password based, such as PGP and RSA encryption algorithms) and file systems (e.g., disk and database file systems) can be implemented by the rights management service and file system, respectively.

In step 5, the packet encoding service retrieves the encrypted objects, chunks or "packetizes" the objects pursuant to a predefined packet scheme (e.g., TCP/IP), and assigns a manifest to each object.

In step 6, the multicast endpoint service then broadcasts the data packets onto the network using multicast IP (e.g., reliable multicast transmission, such as MTP). In general, other components included in the PACS, such as imaging archives, clinicians' workstations, and radiologist reading stations, all have broadcast receiving services that correspond to the multicast IP transmission techniques employed by the multicast endpoint service.

In step 7, the receiver service agents of the various imaging archives, clinicians' workstations, and/or radiologist reading stations receive the multicast broadcasts from the multicast endpoint service. These receiver service agents read the manifest and re-assemble the medical objects locally on the workstations, archives, and other storage mediums.

At step 8, as medical objects are viewed, the user is authenticated against the rights management license store to ensure they have privileges to view or change the medical objects. At this point, the objects are decrypted for viewing. In one such embodiment, the objects are decrypted within the stream for viewing.

System Architecture

Figure 2:
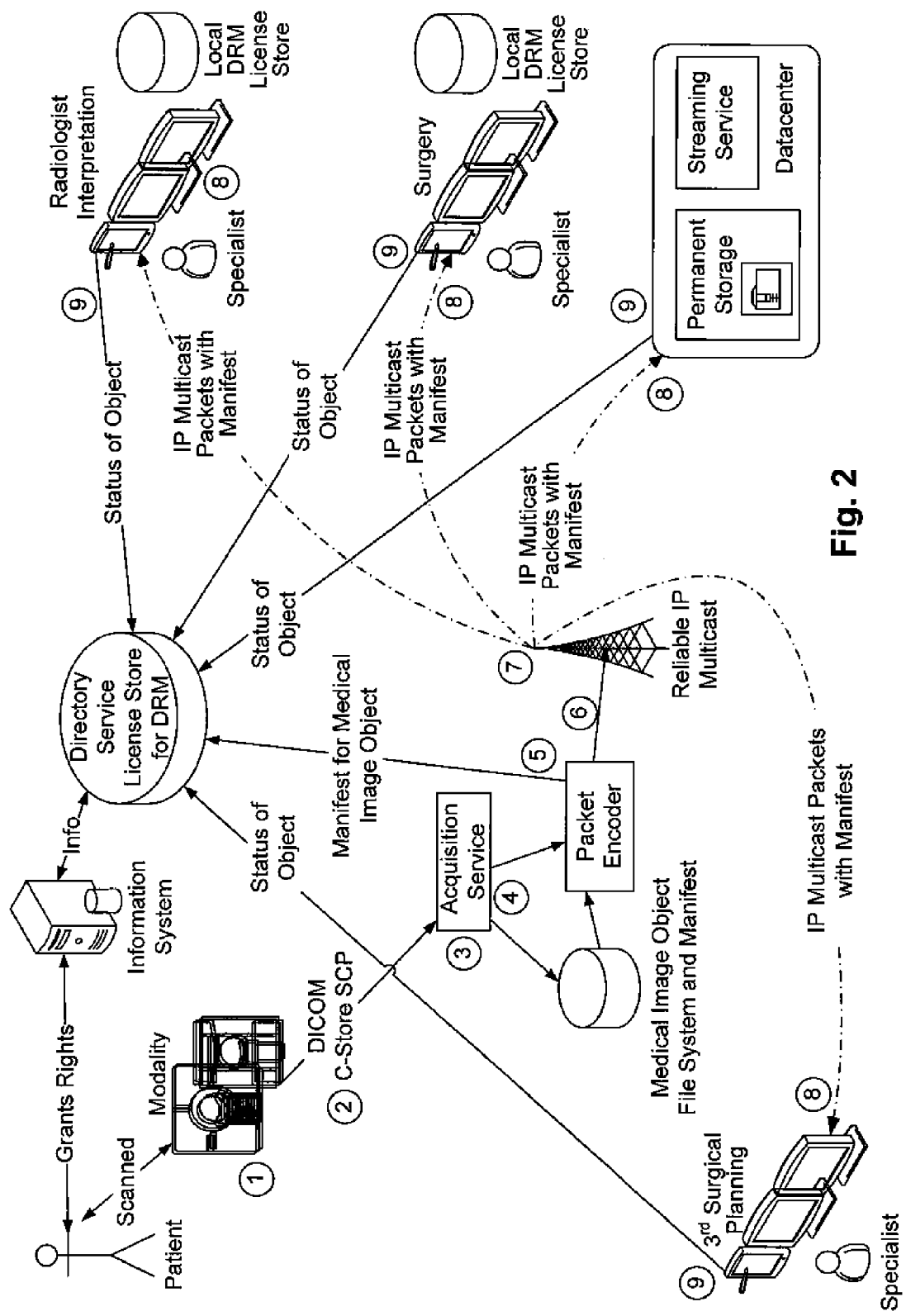
FIG. 2 illustrates a high-level view of a PACS configured in accordance with one embodiment of the present invention.

FIG. 2 illustrates a high-level view of a PACS configured in accordance with one embodiment of the present invention. Each of the system components, as well as medical image object distribution, will be discussed in turn with reference to one or more of the 9 stages depicted. Note that the stages are not intended to implicate any particular processing order.

At stage 1, the patient is scanned by the modality. At this time, the patient or caregiver generates a list of who has been "granted rights" to view the medical image objects that will be generated. Alternatively, or in addition to, the associated system can automatically generate the list of granted rights (e.g., radiology information system automatically generates list to include attending, technician, an other relevant caregivers based on patient consent). This automatically generated list may be edited based on patient and/or doctor input (e.g., via an "Edit Granted Rights" graphical user interface). Typically this list would include the radiology technicians (at least for a brief period of time) and the radiologists and any other specialists that may need to use these medical image objects for interpretation and surgical/care giving scenarios. This list of granted rights is generally referred to herein as an issuance license, and can be temporarily stored in the information system (e.g., secure PC or server within healthcare provider facility, or a memory stick, or a diskette or other suitable storage device that can be used to hold the issuance license) until the physical medical image objects are generated by the scanner. Recall that the granted rights can be time-limited if so desired.

At stage 2, the DICOM-based modality transmits the medical images to the acquisition service.

At stage 3, the acquisition service is configured to perform a normal DICOM C-Store SCP. However, this could also be Twain, secondary capture, or other medical image object acquisition. At this point, the acquisition service can query the information system for the issuance license described in stage 1. Alternatively, the issuance license can be manually provided to the acquisition service (e.g., by loading the issuance license from a diskette or memory stick into a computing system upon which the acquisition service is executing, or simply entering the issuance license information manually using user input devices, such as keyboard, mouse, and graphical user interface). The medical image objects are then encrypted by the acquisition service and keys are registered. In one embodiment, the acquisition service implements an RSA encryption algorithm for encrypting the medical objects. As previously stated however, numerous protection schemes can be used here, depending on factors such as the desired security level and robustness.

At stage 4, the acquisition service creates a pipeline for the object data and stores the encrypted image data locally on the acquisition service and also streams the encrypted image data through a packet encoder. The packet encoder generates a manifest for the encrypted medical image object. The manifest contains a secure packet version of the medical image object making it available for reliable multicast streaming.

At stage 5, the packet encoder sends the manifest and the medical image object information to a central directory service that is programmed or otherwise configured to index/track the location of all medical image objects within the PACS. This directory service also may include a license store and serve as the rights management service. In one particular embodiment, the central directory service is implemented as described in U.S. patent application Ser. No. 10/997,766 filed Nov. 23, 2004, and titled "Health Care Enterprise Directory" which is herein incorporated in its entirety by reference, along with its priority application U.S. Provisional Application No. 60/525,246 filed Nov. 26, 2003, entitled "Enterprise Data Directory in Support of Diverse Data Types in a Healthcare Information System." The central directory service described therein (e.g., "enterprise directory 100") provides a common integration layer for data management and processing in a healthcare information setting or system that includes multiple disparate medical information systems and heterogeneous data objects of different types (e.g., image and report) and formats.

In one such embodiment, the central directory service is coupled to a number of "subscribing" systems distributed across the healthcare provider's enterprise. Subscribers included in the example system shown in FIG. 2 include the permanent storage of datacenter, surgical planning specialist workstation, surgery specialist workstation, radiologist specialist workstation. These subscribing systems receive, generate, or otherwise access information about various data objects (e.g., medical image objects), and regularly transmit updates about the status of these data objects in the form of notifications to the central directory service. The central directory service processes these notifications and maintains an index of data objects and status data about the objects. The index includes, for example, references to the data objects such as pointers to local repositories associated with the subscribing systems. Alternatively, or in addition to, references may point or otherwise refer to copies of the digital data objects that have been provided to the central directory service and stored in one or more data archives or stores (e.g., datacenter). The central directory service notifies one or more subscribing systems of status changes reflected in notifications provided to it. The central directory service may broadcast messages or alerts to one or more subscribing systems according to predetermined instructions or logic that dictate, for instance that status updates concerning a specified patient be provided to a specific subscribing system. A user of a subscribing system can access one or more data objects referenced in such a message through the central directory service. The user can also provide instructions and preferences regarding messages and notifications exchanged between a subscribing system and the central directory service, as well as audit or other information to be used by the directory service.

At stage 6, medical image packet data is pipelined from the packet encoder to the network stack for reliable multicast IP. As previously discussed, any number of multicast technologies can be used here, and reliable multicast IP is one example embodiment. At stage 7, the medical image object packets with manifest are broadcast to all available listeners. The type of multicast used will depend on factors such as the communication medium and protocols employed and the desired level of reliability. Note that TCP/IP protocols work well for transmission over both LAN (e.g., Ethernet) and WAN (e.g., Internet).

At stage 8, the medical image object listeners (e.g., permanent storage of datacenter, surgical planning specialist workstation, surgery specialist workstation, radiologist specialist workstation) receive the broadcast manifest and re-assemble the medical image objects locally from the instructions of the manifest. These medical image objects are then stored locally for use on the computer, for example, in an isolated protected file system. In one particular embodiment, if local storage hits a watermark threshold, the listener processing system deletes the oldest medical image objects and notifies the directory service.

At stage 9, the medical image object listeners notify the directory service that the medical image object is on the local computer (status of object). Note that this status can be updated, for example, should an object be removed by user or by operation of a threshold-based self-cleaning process that eliminates older files to make room for newer objects (as previously described). In any case, the directory service knows where all images are on the system at any one time. During any access on the local computer, the user must authenticate with the rights management service and the end-user (receiver) solution uses the issuance license to decrypt the medical image objects for viewing. Thus, digital rights management is enabled to protect the distributed and stored objects and the patient's privacy.

Acquisition with DRM Process

Figure 3:
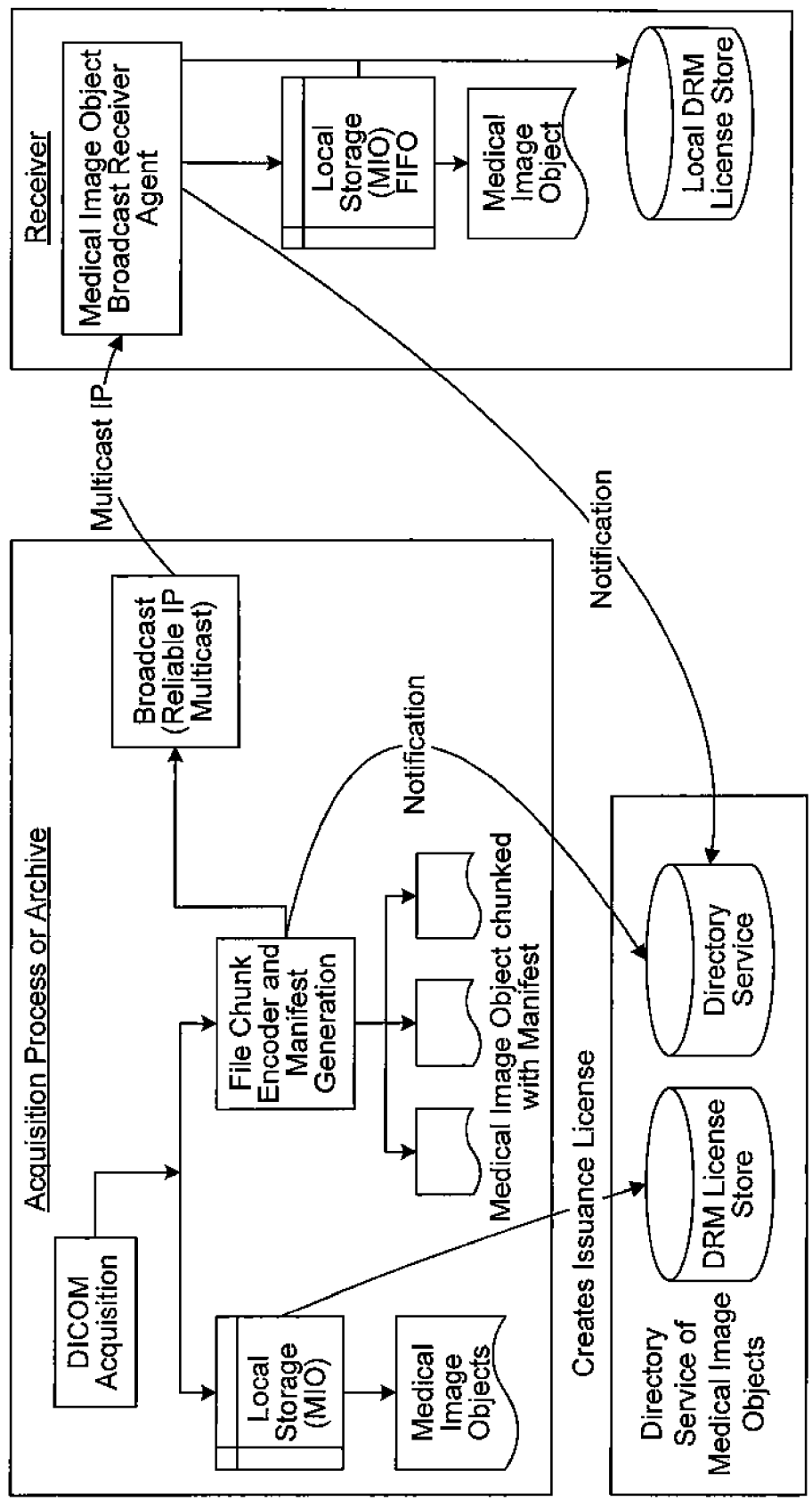
FIG. 3 illustrates a detailed bock diagram and communication flow of a PACS utilized during an image acquisition process, in accordance with one embodiment of the present invention.

FIG. 3 illustrates a components and communication flow of a PACS utilized during an image acquisition process, in accordance with one embodiment of the present invention.

As can be seen, the system includes an acquisition process/archive section, a receiver section, and a directory service section. The receiver section can be a data storage or archive sub-system (e.g., permanent off-site storage) or a specialist's workstation (e.g., interpreter/radiologist). As will be appreciated in light of this disclosure, a plurality of receiver can be configured to communicate with the acquisition process/archive section and the directory service section. Each of the functional modules can be implemented, for example, in software (e.g., C, C++, or other object-oriented instruction set). Also, storage facilities can be implemented using any conventional storage techniques, such as dedicated storage devices (e.g., hard drives, servers, ROM, flash memory, etc) or virtual storage.

This example embodiment shown in FIG. 3 assumes a DICOM-based modality transmits the medical images to a DICOM acquisition service in a TCP stream. The DICOM acquisition service converts the TCP stream of data into DICOM objects, encrypts the objects, and generates encrypted objects. The DICOM acquisition service uses a local storage process to store the encrypted medical image object (MIO) in local storage. The local process also creates the issuance license (e.g., based on input specifying access rights from a user, such as patient and/or healthcare provider via a graphical user interface or other suitable data input mechanism) and stores it in the DRM license store of the directory service. The DICOM acquisition service also streams the encrypted MIO data through a packet encoder. As previously explained, the packet encoder effectively breaks each MIO (or any other type of file) into chunks, and generates a manifest for the encrypted MIO. The manifest contains a secure packet version of the medical image object making it available for reliable multicast streaming or other broadcast.

In this example embodiment, the output of the packet encoder is provided to a number of archive/storage facilities included in the acquisition process/archive, and is also broadcast via reliable multicast IP to one or more receivers. In addition, the packet encoder sends a notification (e.g., including manifest and the medical image object information) to the directory service, which is configured to index/track the location of all medical image objects within the system as previously explained. The directory service also includes the DRM license store and operates as the rights management service as previously explained.

The medical image object packets with manifest are broadcast to the receiver, and the receiver includes a medical image object receiver agent configured to receive the broadcast manifest and re-assemble the medical image objects locally from the instructions of the manifest. The receiver agent then sends a notification to the directory service to indicate that it has received new object data. In this sense, the receiver agent is actually a transceiver (both receive and send functions are enabled). The re-assembled medical image objects (or other broadcast data objects) are then stored locally using a local storage process, so that they can be viewed or otherwise securely used on the computer/workstation. In the embodiment shown, the local storage process is configured to implement a FIFO storage. If the local storage facility exceeds it max capacity, then the local process effectively deletes or pushes out the oldest medical image objects to make room for newly received medical image objects and/or other patient data. The local process may also be configured to send (e.g., via itself or the receiver agent) a notification to the directory service that it has received new object data, and/or that it has deleted old object data.

Variations on this embodiment will be apparent in light of this disclosure. For instance, note that functionality of the local storage process can be integrated into the MIO broadcast receiver agent (or vice versa), if so desired. In any case, the directory service knows all images stored on the receiver at any one time. In addition, the receiver agent and/or the local process have access to the local DRM license store, which stores directory service data relevant to that receiver (including object status). Secure distributed database and replication techniques can be used to synchronize the local DRM license store of the receiver with the DRM license store of the directory service. Alternatively, dedicated secure transmissions can be used to communicate DRM information between DRM license stores. Alternatively, each DRM store can be manually maintained (e.g., by system administrator). Other information, such as cryptography keys, passwords, etc, can also be stored in the DRM license store to facilitate carrying out a robust DRM scheme.

During any access attempts of the stored medical image objects, the local process (or other such process) requires the user to authenticate (e.g., user name and password or other secure ID mechanism) with the rights management service of the directory server, and uses the issuance license (which specifies who has been granted rights to access the object data) to decrypt the medical image objects for viewing. Security information such as the issuance license and cryptography keys can be exchanged between the acquisition process/archive and the receiver, for example, by a manual exchange process, secure transmission, or other suitable means. In one particular embodiment, the issuance license is stored in the DRM license store of the directory service, which is then securely replicated to the receiver DRM license stores, using any number of conventional or custom replication processes.

The foregoing description of the embodiments of the invention has been presented for the purposes of illustration and description. It is not intended to be exhaustive or to limit the invention to the precise form disclosed. Many modifications and variations are possible in light of this disclosure. For example, embodiments of the present invention can be used to facilitate the transmission and storage of data objects other than medical image objects using reliable multicasting, including various types of data or pieces of information, such as video files, audio files, non-medical images, on-line forms, documents in PDF, TIFF, BITMAP, GIF, JPEG, and various other formats, including textual, tabular, graphical, HTML, or XML formats. Example medical data objects includes, for example, a radiology image, a dictation voice clip, a scanned Advance Beneficiary Notice (ABN) form, or an electrocardiogram (ECG) strip. Other data objects will be apparent in light of this disclosure. It is intended that the scope of the invention be limited not by this detailed description, but rather by the claims appended hereto.

What is claimed is:

1. A method of protecting patient information communicated over a data network and stored at a subscribing workstation, the method comprising:

receiving patient information, including medical image data from a medical imaging device;

converting the patient information into medical image object (MIOs) in a computing system of an acquisition system;

encrypting the MIOs in the computing system;

creating an issuance license in the computing system that specifies access rights of the MIOs, thereby limiting future access to the MIOs wherein the issuance license is stored in a central directory service;

chunking the encrypted MIOs in the computing system into packets, wherein each of the packets is encrypted, and assigning a manifest to each chunked MIO; and simultaneously broadcasting the manifest across the data network to a plurality of subscribing workstations on the data network;

simultaneously broadcasting the encrypted MIO packets across the data network to the plurality of subscribing workstations on the network;

receiving the broadcast manifest and encrypted MIO packets at the subscribing workstations, and re-assembling the MIOs at each of the subscribing workstations from instructions included in the manifest;

storing the reassembled MIOs locally at each of the subscribing workstations;

sending a first notification from at least one of the subscribing workstations to the central directory service, the first notification identifies that the MIOs have been received and stored by the subscribing workstation that sent the first notification;

sending a second notification from at least one of the subscribing workstations to the central directory service, the second notification identifies that the MIOs have been deleted from the subscribing workstation that sent the second notification;

tracking, with the central directory service, the MIOs currently stored at each of the subscribing workstations of the plurality of subscribing workstations based on the received first and second notifications; and requiring user authentication in accordance with the issuance license prior to locally decrypting the MIOs at a subscribing workstation for user access.

2. The method of claim 1, further comprising:

storing the issuance license in a digital rights management (DRM) license store of the central directory service;

communicatively connecting each of the plurality of subscribing workstations on the network to the DRM license store; and receiving, with the plurality of subscribing workstations on the network, the issuance license from the DRM license store, wherein the central directory service further tracks issuance licenses for each of the MIOs currently stored at each of the subscribing workstations.

3. The method of claim 1, further comprising:
storing the encrypted MIO packets in an archive for long term storage.

4. The method of claim 1, further comprising:
deleting an older MIO stored locally at at least one subscribing workstation to make room for the broadcast MIO; and
maintaining a directory service record of the MIOs currently stored at each of the subscribing workstations on the central directory service;
notifying the central directory service of the deleted MIO from storage from the at least one subscribing workstation; and
updating the directory service record to remove the deleted MIO from the directory service record of the MIOs currently stored at the at least one subscribing workstation.

5. The method of claim 1, wherein converting the patient information into MIOs includes converting the patient information into Digital Imaging and Communications in Medicine (DICOM) MIOs.

6. The method of claim 1, wherein broadcasting the manifest and encrypted MIO packets is carried out using reliable internet protocol (IP) multicasting.

7. A system for securely communicating medical information, comprising:
a first storage medium having stored therein a plurality of executable instructions, wherein when executed, the instructions operate the system to:
receive patient information, including medical image data from a medical imaging device;
convert the patient information into medical image object (MIOs) in a computing system of an acquisition system;
encrypt the MIOs in the computing system;
create an issuance license that specifies access rights of the MIOs, thereby limiting future access to the MIOs;
chunk the encrypted MIOs into packets in the computing system, wherein each of the packets is encrypted, and assigning a manifest to each chunked MIO;
simultaneously broadcast the manifest across a data network to a plurality of subscribing workstations on the data network; and
simultaneously broadcast the encrypted MIO packets across the data network to the plurality of subscribing workstations on the network; and
a first processor coupled to the at least one storage medium to execute the instructions;
a second storage medium of one of the subscribing workstations having stored therein a plurality of executable instructions, wherein when executed, the instructions operate the system to:
receive the broadcast manifest and encrypted MIO packets at one or more of the plurality of receivers and re-assemble the MIOs from instructions included in the manifest;
store the reassembled MIOs locally to the subscribing workstation
send a first notification of the received and stored MIOs;
send a second notification of deleted MIOs from the subscribing workstation;
require user authentication in accordance with the issuance license to decrypt the reassembled MIOs during access attempts of the reassembled MIOs;
a second processor of the subscribing workstation coupled to the second at least one storage medium to execute the instructions;
a third storage medium having stored therein a plurality of executable instructions, wherein when executed, the instructions operate the system as a directory service to:
receive the first notification of the received and stored MIOs from the subscribing workstation;
receive the second notification of the MIOs deleted from the subscribing workstation;
track the MIOs currently locally stored at each subscribing workstation based upon the received first and second notifications;
register the issuance licenses for each of the current locally stored MIOs; and
a third processor coupled to the third storage medium to execute the instructions and operate as a directory service.

8. The system of claim 7, wherein when executed, the instructions of the third storage medium further operate the system to:
store the issuance license in a digital rights management (DRM) license store of the directory service; and
transmit the issuance license from the directory service to a subscribing workstation at which the MIOS are currently locally stored.

9. The system of claim 7, wherein when executed, the instructions of the second storage medium further operate the system to:
remove older MIOs, stored local to each of the receivers to make room for the stored reassembled MIOs; and
send the second notification to the directory service indicating the change in MIO storage.

10. The system of claim 7, wherein the system converts the patient information into MIOs by converting the patient information into Digital Imaging and Communications in Medicine (DICOM) MIOs.

11. The system of claim 7, wherein the system broadcasts the manifest and encrypted MIO packets using reliable IP multicasting.

* * * * *